US008882271B2

(12) United States Patent
Sander

(10) Patent No.: US 8,882,271 B2
(45) Date of Patent: Nov. 11, 2014

(54) SURGICAL MICROSCOPE SYSTEM FOR OPHTHALMOLOGY, AND ASSOCIATED DETECTION UNIT

(71) Applicant: Leica Microsystems (Schweiz) AG, Heerbrugg (CH)

(72) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 217 days.

(21) Appl. No.: 13/707,994

(22) Filed: Dec. 7, 2012

(65) Prior Publication Data

US 2013/0148080 A1    Jun. 13, 2013

(30) Foreign Application Priority Data

Dec. 8, 2011    (DE) .......................... 10 2011 088 039

(51) Int. Cl.
*A61B 3/14*    (2006.01)
*A61B 3/10*    (2006.01)
*A61B 3/13*    (2006.01)

(52) U.S. Cl.
CPC .. *A61B 3/102* (2013.01); *A61B 3/13* (2013.01)
USPC ........................................................ 351/206

(58) Field of Classification Search
USPC ...................... 351/206, 220, 205, 246; 606/4; 356/479; 359/380, 368, 372, 373
See application file for complete search history.

(56) References Cited

U.S. PATENT DOCUMENTS

2011/0279821 A1    11/2011    Brennan et al.
2012/0092615 A1*   4/2012    Izatt et al. ..................... 351/206

FOREIGN PATENT DOCUMENTS

WO    03/009745 A2    2/2003

OTHER PUBLICATIONS

Drexler, Wolfgang, et al., Optical Coherence Tomography—Technology and Applications, Preface and Table of Contents Springer, 2008.
Geerling, Gerd, et al., Intraoperative 2-Dimensional OPtical Coherence Tomography as a New Tool for Anterior Segment Surgery, Arch. Ophthalmol., vol. 123, No. 2, Feb. 2005, pp. 253-257.

* cited by examiner

*Primary Examiner* — Hung Dang
(74) *Attorney, Agent, or Firm* — Hodgson Russ LLP

(57) ABSTRACT

A surgical microscope system (100) for ophthalmology, in particular for cataract surgery, comprising a surgical microscope (10) having an optical viewing unit (13), is proposed, in which an optical coherence tomograph (20) is set up to scan at least a region of a lens (53) of an eye (50) and to generate scan values, and in which a detection unit (30) is set up to generate, on the basis of the scan values, diagnostic data that correspond to light-reflecting structures in the scanned region of the eye (50) and that derive from a plane of the eye (50) that corresponds to an object plane of the surgical microscope (10).

13 Claims, 1 Drawing Sheet

SURGICAL MICROSCOPE SYSTEM FOR OPHTHALMOLOGY, AND ASSOCIATED DETECTION UNIT

CROSS REFERENCE TO RELATED APPLICATIONS

Figure 1:
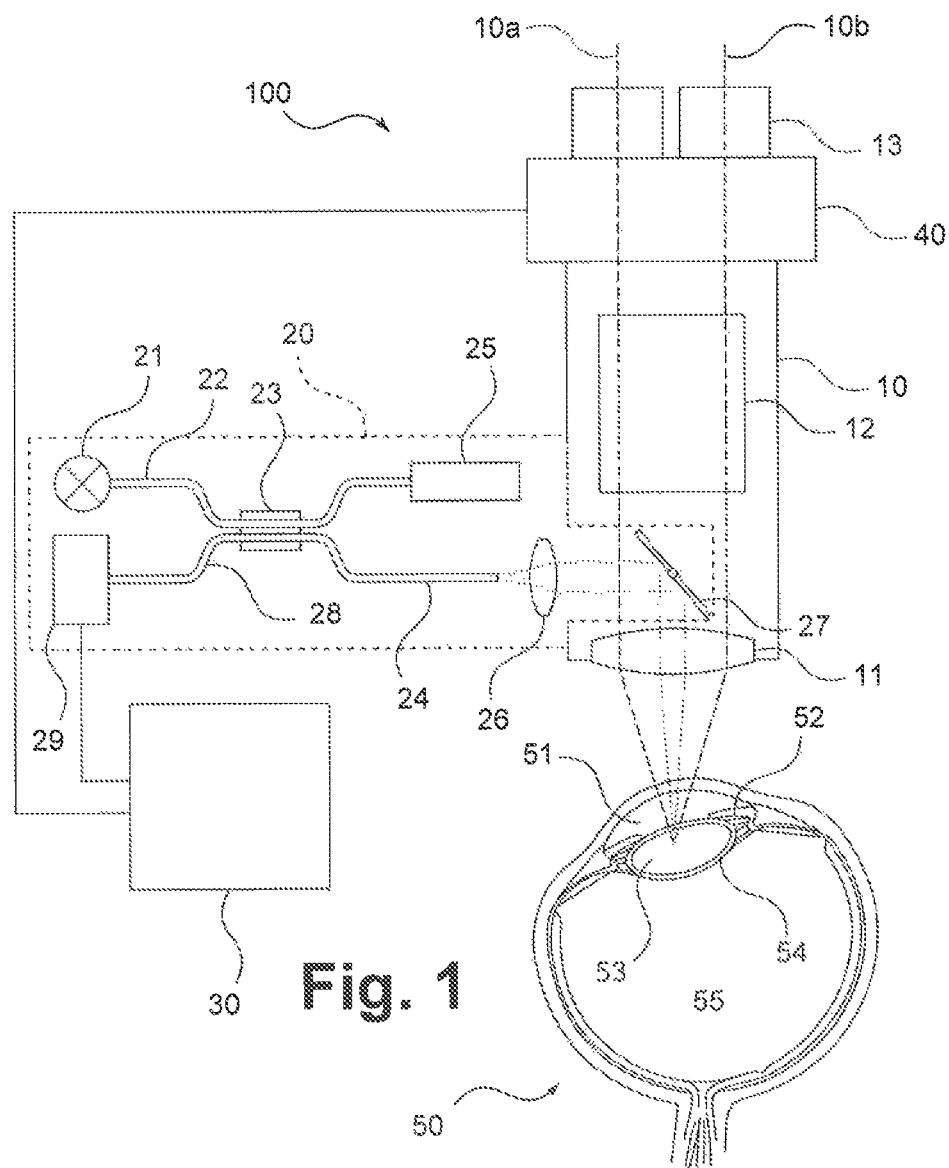

This application claims priority of German patent application number 10 2011 088 039.9 filed Dec. 8, 2011, the entire disclosure of which is incorporated by reference herein.

FIELD OF THE INVENTION

The present invention relates to a surgical microscope system for ophthalmology, in particular for the investigation and/or surgical treatment of a cataract of an eye, and to a detection unit for a surgical microscope system of this kind comprising the use of an optical coherence tomograph.

BACKGROUND OF THE INVENTION

The term "cataract" refers to a turbidity of the lens of the eye, i.e. a decrease in its transparency. Certain forms of cataracts develop relatively quickly, but the great majority develop over a period of several decades. Severe forms of cataracts therefore occur principally in older people. Surgical methods for the removal of cataracts have been known for some time, and represent routine procedures. The lens is usually replaced in this context by a plastic lens (intraocular lens, IOL).

In almost all forms of cataracts, the impairment in vision is due not to increasing opacity of the lens and thus to increased light absorption, but instead to a structural change in the lens that results in increased light scattering. This light scattering causes a decrease in the contrast of the field of vision.

Cataract surgery is not entirely risk-free. Because cataracts develop slowly, the question as to the correct time for an operation is therefore in some circumstances difficult to answer.

In a cataract operation, the lens body is as a rule disintegrated, removed, and replaced by a plastic lens. The lens capsule remains in the eye. After lens removal, the surgeon attempts to remove remaining lens residues as completely as possible by means of the aforementioned capsule polishing. At present, the posterior lens capsule is cleaned largely by feel, and in accordance with the subjective assessment and experience of the surgeon.

For stability reasons, the posterior capsule of the lens of the eye is not removed in the cataract procedure. Serious complications can otherwise occur. On the other hand, fibrous proliferation of certain cells ("capsular fibrosis") can occur on the posterior lens capsule that remains after the operation, causing turbidity to reoccur. Visual impairments can also, however, arise principally because lens residues or very thin membranes remain behind on the posterior lens capsule. An "after-cataract" of this kind forms in up to 30% of cases after a cataract operation. The exact causes are not completely known; this is also due to an absence of objective measurement methods, for example to check the surgical outcome. Further operations or laser treatments are necessary in order to remove the after-cataract.

Lens residues are transparent media, however, and are very difficult to detect. Capsule polishing moreover represents a very severe stress for the capsule, which can thereby be damaged. It is therefore of interest to detect remaining lens residues, especially intraoperatively, in order to avoid a possible after-cataract.

No possibility so far exists for intra- or postoperatively sensing and quantifying the state of the posterior lens capsule during the operation. Maximally complete removal of lens residues, membranes, etc., also called "lens polishing," is usually performed exclusively visually, and can therefore lead to the aforementioned residual risk.

In light of this, a need therefore exists for improved surgical microscope systems that offer corresponding diagnostic capabilities.

Optical coherence tomography (OCT) represents a diagnostically valuable optical image-producing method especially in biomedical optics and in medicine. A comprehensive review of the existing art is provided, for example, in W. Drexler and J. G. Fujimoto (eds.), "Optical Coherence Tomography. Technology and Applications," Springer, 2008.

Optical coherence tomography makes possible high-resolution cross-sectional depictions of the internal microstructure of biological tissue by measuring light that is reflected at interfaces at different depths. Unlike methods such as ultrasonic tomography, optical coherence tomography is non-contact and therefore does not stress the patient. Corresponding structures can be sensed in real time and at a resolution of 1 to 15 µm, i.e. approximately two orders of magnitude higher than with ultrasound.

In optical coherence tomography, low-coherence light of a corresponding light source is split at a beam splitter of an interferometer, e.g. a Michelson interferometer, into a reference arm and a measurement arm. Light of the reference arm is reflected at a corresponding mirror, and light of the measurement arm at a structure of the object being investigated.

After reflection at the respective surfaces, the signals of the reference arm and measurement arm are overlaid. Interference between the signals of the two arms yields a pattern from which the relative optical path length can be derived. A corresponding depth profile measurement is also referred to as an "axial scan" (A-scan). As a rule an optical coherence tomograph has a scanning device, so that a corresponding sample can also be scanned transversely in one or two directions. The two-dimensional scan that is obtained extends parallel to the axial scan as a perpendicular section through the eye, and is called the B-scan. The three-dimensional scan that is obtained is called the C-scan.

The interior of the eye is substantially transparent, and in the healthy state therefore transmits light of corresponding wavelengths with only minimal optical attenuation and scattering. Optical access both to the anterior segment and to the ocular fundus is therefore generally good. Ophthalmologic imaging, in particular of the retina, was therefore one of the first areas of application of optical coherence tomography. Optical coherence tomography makes possible, for example, early diagnosis of retinopathies and macular degeneration.

Specifically adapted coherence tomographs are used to investigate the anterior region of the eye. They must ensure a sufficiently high scanning rate (e.g. 4,000 A-scans per second) that even relatively large-area structures can be sensed within an acceptable time. Light sources having suitable wavelengths must also be used, since the healthy eye is almost transparent to the wavelengths (for example, 830 nm) usually utilized for coherence tomography of the ocular fundus. Light having a wavelength of, for example, 1310 nm is therefore used for corneal investigation.

The areas of application of optical coherence tomography in the anterior region of the eye encompass in particular measurement of corneal thickness, evaluation of narrow-angle glaucoma, and measurement of the anterior chamber of the eye. Reference is made in this context to the article "Interoperative Two-Dimensional Optical Coherence Tomography as a New Tool for Anterior Segment Surgery," Gerd Geerling et al. (reprinted), ArchOphthalmol Vol. 123, February 2005.

In systems of this kind, lateral scanning can occur in the form of a so-called sector scan (diverging), a right-angle or telecentric scan (using a parallel-shifted measurement arm), or in converging fashion.

SUMMARY OF THE INVENTION

The present invention provides a surgical microscope system for ophthalmology, in particular for the investigation and/or surgical treatment of a cataract of an eye, as well as a detection unit for a surgical microscope system of this kind. The surgical microscope system comprises a surgical microscope having an optical viewing unit, and also comprises an optical coherence tomograph and a detection unit.

The optical coherence tomograph is set up to scan at least a region of a lens of an eye and to generate scan values, and the detection unit is set up to generate, on the basis of the scan values, diagnostic data that correspond to light-reflecting structures in the scanned region. The detection unit is further set up to determine the diagnostic data in a plane of the eye that corresponds to an object plane of the surgical microscope.

The surgical microscope system may further have a superimposition unit that is set up to superimpose the diagnostic data into the surgical microscope for optical viewing by means of the optical viewing unit.

The present invention proceeds from a known surgical microscope having an optical coherence tomograph.

The present invention is based on the recognition that optical coherence tomography can also be used with advantage for intra- and postoperative evaluation of sufficient removal of lens residues or membranes on the posterior lens capsule.

According to the present invention, an optical coherence tomograph is therefore provided as part of a surgical microscope. It is set up to scan at least a region of a lens of an eye, and to generate corresponding scan values. A "region of a lens of the eye" is to be understood in the context of this Application as the anterior region of the eye, in which, in the healthy state prior to surgery, the lens of the eye is located. In a cataract operation, the lens of the eye is removed from the region and only lens residues may possibly remain in the otherwise empty region. A plastic lens that is subsequently inserted is also located in the "region of a lens of the eye."

A detection unit according to the present invention is likewise provided as part of the surgical microscope system. This is set up to generate diagnostic data on the basis of the scan values. These are correlated with light-reflecting structures in the scanned region of the eye. Such "structures" can be structures of the natural lens of the eye, of the posterior lens capsule, or of the intraocular lens, i.e. in general of the anterior segment of the eye. The term "structures" can therefore also encompass reflective interfaces or components of an artificial lens.

According to the present invention a data set (hereinafter referred to as a "D-scan"), which represents diagnostic data from a plane of the eye that in turn corresponds to an object plane of the surgical microscope, is generated from the acquired diagnostic data of the optical coherence tomograph. The calculated "D-scan" thus constitutes diagnostic data that represent a horizontal section through the eye, i.e. a section perpendicular to the B-scan. The "D-scan" can be selected, in particular, so that it corresponds to the particular object plane of the surgical microscope being viewed. The object plane of a microscope is, as is known, the focal plane that is located in the object being investigated and is in turn perpendicular to the optical axis of the main objective.

If image data are generated as diagnostic data, the "D-scan" thus represents a two-dimensional horizontal sectional image (perpendicular to a B-scan). An image generated in this fashion thus represents data from the optical coherence tomograph that derive from a plane which corresponds to a specific object plane (in particular, the specific one being viewed) of the surgical microscope.

The "D-scan" can be calculated from multiple A-scans, multiple B-scans, or a C-scan. If image data are used as diagnostic data of the "D-scan," the surgeon then has available, in particularly favorable fashion, two types of image information, namely on the one hand data from the optical coherence tomograph and on the other hand those from the surgical microscope. He or she can thus view not only the optically imaged object plane but also the light-reflecting structures sensed in the same plane by the optical coherence tomograph.

A surgical microscope system advantageously encompasses an optical coherence tomograph that comprises at least one light guide and/or at least one interferometer having a 2×2 coupler. An interferometer, e.g. a Michelson interferometer, can be implemented particularly easily and simply using light-guide technology.

A surgical microscope system in which the detection unit is set up to sense a position and/or a magnitude of a natural or artificial lens of the eye present in the scanned region of the eye is particularly advantageous. Sensing of the position of an inserted plastic lens from a "D-scan" is particularly advantageous because this makes possible largely automatic monitoring of the surgical outcome.

It is especially advantageous in this context to generate corresponding data at least largely automatically, so that further user interventions are not necessary and the surgeon can devote him- or herself exclusively to the operation, for example to insertion of the plastic lens.

The detection unit according to the present invention for use in a corresponding surgical microscope system benefits in the same fashion from the advantages explained previously.

Further advantages and embodiments of the invention are evident from the description and the appended drawings.

It is understood that the features recited above and those yet to be explained below are usable not only in the respective combination indicated, but also in other combinations or in isolation, without departing from the scope of the present invention.

BRIEF DESCRIPTION OF THE DRAWING VIEW

The invention is depicted schematically in the drawing on the basis of an exemplifying embodiment, and will be described in detail below with reference to the drawing.

FIG. 1 shows a surgical microscope system according to a particularly preferred embodiment of the invention.

DETAILED DESCRIPTION OF THE INVENTION

In FIG. 1, a surgical microscope system according to a particularly preferred embodiment of the invention is depicted schematically and labeled 100 in its entirety. It encompasses a surgical microscope 10 that is embodied in a manner known per se.

Surgical microscope 10 is embodied as a stereomicroscope, and comprises two beam paths 10a, 10b for the two eyes of an observer, and a common objective 11. Further optical components 12, designated only in part, are provided in known fashion. Surgical microscope 10 further has a viewing unit 13, for example in the form of a pair of eyepieces.

Surgical microscope 10 is set up for focused viewing of a focal point in an eye 50, which is depicted in FIG. 1 at disproportionately large scale. The eye encompasses, inter alia, an anterior eye chamber 51, a posterior eye chamber 52, a lens 53 of the eye having a posterior lens capsule 54, and a vitreous body 55. Surgical microscope system 100 is set up to view a region of lens 53 of the eye.

An optical coherence tomograph 20 is embodied as part of surgical microscope system 100. It encompasses a light source 21 that is embodied to generate light of (a) suitable wavelength(s). Advantageously, an optical coherence tomograph, having a light source that generates light having a wavelength from 800 to 1400 nanometers, in particular from 850 to 1000 nanometers, is provided. As mentioned, the healthy, unclouded structures of the eye are transparent to such wavelengths all the way to the fundus, so that, for example, lens residues can then be detected particularly effectively.

In the embodiment depicted in FIG. 1, optical coherence tomograph 20 encompasses a light guide system; an interferometer can, however, likewise be embodied e.g. in conventional fashion, i.e. with semitransparent mirrors.

The light of light source 21 is coupled into a light guide 22. An interferometer is realized by means of a coupler 23, for example a 2×2 coupler of known type. In this interferometer, the incoupled light is split into a measurement arm 24 and a reference arm 25. Reference arm 25 possesses components (not described further), for example mirrors, that define a reference path for the light.

Light in measurement arm 24 passes through a schematically depicted optic 26 and is used by means of a scanning device 27 to scan the region to be investigated. Scanning device 27 can be embodied, for example, as a mirror tiltable in multiple directions. Optic 26 is embodied to compensate for any changes in path length that may be caused thereby.

In FIG. 1, optical coherence tomograph 20 is arranged in such a way that scanning device 27 is arranged between objective 11 of surgical microscope 10 and zoom system 12. An arrangement in which scanning device 27 is arranged between eye 50 and objective 11, or behind zoom system 12 (as seen from objective 11), is alternatively possible.

After being reflected at the corresponding mirrors or structures and overlaid in coupler 23, the light is coupled by means of a light guide 28 into a detector 29, in which corresponding scan values are generated.

A detection unit 30 is connected to detector 29, for example via corresponding cables or by radio, and generates diagnostic data from the scan values. This is accomplished, for example, by the fact that detection unit 30 correlates or combines scan values of multiple scans with one another, and thereby generates sectional image data, in particular "D-scan" data, or three-dimensional diagnostic data. Detection unit 30 can also be set up to produce corresponding numerical data, for example by integration.

In a particularly advantageous surgical microscope system, the detection unit is set up to generate the diagnostic data as numerical data. The numerical data correspond to a total quantity of light-reflecting structures in at least one part of the scanned region of the eye. Numerical data can encompass in this context, for example, a percentage that indicates to the surgeon the extent to which lens residues have been removed. This can serve to ensure that lens polishing is performed only to a necessary extent that not yet does damage to the lens capsule. Numerical values represent, for the first time, reliable and objective data that are usable, for example, for studies regarding the probability of an after-cataract.

For this purpose, the detection unit is advantageously set up to generate the diagnostic data by integrating over at least one part of the scanned region of the eye. Light-reflecting structures are integrated in this context. For example, an integral summed over grayscale values of a corresponding sectional image or three-dimensional image can be created. Because light-reflecting structures have grayscale values differing from those of transparent regions, regions having light-reflecting structures and regions not having such structures have different summed integrals. Different weighting factors, which for example heavily weight large-area structures, can likewise be used. This makes possible particularly differentiated pre-, intra-, and postoperative diagnosis.

A superimposition unit 40 is provided and is connected in corresponding fashion to detection unit 30. Superimposition unit 40 superimposes the diagnostic data that were generated by detection unit 30 into the surgical microscope for viewing by means of viewing unit 13. Detection unit 30 can also possess means (not depicted) for otherwise outputting or storing the diagnostic data. In particular, detection unit 30 can be connected to zoom system 12 in order to pick off the respective microscope magnification. This ensures correctly scaled superimposition of, for example, image data of a "D-scan" onto the microscope image.

Multiple "D-scans" can of course also be assembled into a three-dimensional diagnostic data image of the anterior segment of the eye, or a portion thereof. This allows complete sensing and/or documentation of the structures that are present or that remain, in particular after lens polishing has been completed.

Advantageously, the surgical microscope system 100 according to the present invention comprises the superimposition unit 40. Superimposition unit 40 is set up to superimpose the diagnostic data into the surgical microscope 10 for optical viewing by means of the optical viewing unit 13. Advantageously, superimposition can be switched in and out of the surgical microscope 10. The surgeon can thus continuously monitor the progress and outcome of the procedure, pre-, intra-, and postoperatively, during the entire surgical procedure. He or she can perform an optical investigation during the procedure, and need not look away from the object in order to view the diagnostic image on separate data media. Alternatively or additionally, however, a presentation of the diagnostic data on an external display device (not shown), for example a monitor, is also possible. This allows third parties to observe as well. Recording of the diagnostic data on suitable data media, for example for logging and/or documentation of a surgery, is likewise possible.

Superimposition of the diagnostic data, in particular of a diagnostic data image, occurs usefully onto both binocular eyepieces of the surgical microscope's optical viewing unit 13, over or also alongside the corresponding microscope images, or as a so-called correlated overlay with the microscope image; care must be taken here that the respective image data are overlaid identically in terms of location and magnification, i.e. congruently.

PARTS LIST

10 Surgical microscope
10a Beam path
10b Beam path
11 Objective
12 Zoom system
13 Viewing unit 20 Optical coherence tomograph
22 Light guide
23 Coupler
24 Measurement arm
25 Reference arm
26 Optic
27 Scanning device
28 Light guide
29 Detector
30 Detection unit
40 Superimposition unit
50 Eye
51 Anterior chamber of eye
52 Posterior chamber of eye
53 Lens of eye
54 Posterior lens capsule
55 Vitreous body
100 Surgical microscope system

What is claimed is:

1. A surgical microscope system (100) for cataract surgery comprising:
   a surgical microscope (10) having an optical viewing unit (13);
   an optical coherence tomograph (20) configured to scan at least a region of a lens (53) of an eye (50) and to generate scan values; and
   a detection unit (30) configured to generate, on the basis of the scan values, diagnostic data that correspond to light-reflecting structures in the scanned region;
   wherein the detection unit (30) is further configured to determine the diagnostic data in a plane of the eye (50) that corresponds to an object plane of the surgical microscope (10).

2. The surgical microscope system (100) according to claim 1, further comprising a superimposition unit (40) configured to superimpose the diagnostic data into the surgical microscope (10) for optical viewing by means of the optical viewing unit (13).

3. The surgical microscope system (100) according to claim 1, wherein the detection unit (30) is configured to generate the diagnostic data as image data in the form of a sectional image.

4. The surgical microscope system (100) according to claim 1, wherein the detection unit (30) is configured to generate the diagnostic data as image data in the form of a three-dimensional image.

5. The surgical microscope system (100) according to claim 1, wherein the detection unit (30) is configured to generate the diagnostic data as numerical data that correspond to a total quantity of light-reflecting structures in at least one part of the scanned region.

6. The surgical microscope system (100) according to claim 5, wherein the detection unit (30) is configured to generate the diagnostic data by integrating over the at least one part of the scanned region.

7. The surgical microscope system (100) according to claim 1, wherein the optical coherence tomograph (20) includes a light source (21) configured to generate light having a wavelength in a range from 800 to 1400 nanometers.

8. The surgical microscope system (100) according to claim 1, wherein the light source (21) of the optical coherence tomograph (20) is configured to generate light having a wavelength in a range from 850 to 1000 nanometers.

9. The surgical microscope system (100) according to claim 1, wherein the optical coherence tomograph (20) includes at least one light guide (22, 28).

10. The surgical microscope system (100) according to claim 1, wherein the optical coherence tomograph (20) includes at least one interferometer having a 2×2 coupler (23).

11. The surgical microscope system (100) according to claim 1, wherein the detection unit (30) is configured to sense at least one of a position and a magnitude of a natural or artificial lens of the eye present in the scanned region.

12. The surgical microscope system (100) according to claim 11, wherein the detection unit (30) is configured to automatically generate position data and/or magnitude data based on what is sensed.

13. A detection unit (30) for a surgical microscope system (100) having an optical coherence tomograph (20) according to claim 1, the detection unit (30) being configured to generate, on the basis of scanning by the optical coherence tomograph (20), diagnostic data that correspond to light-reflecting structures in the scanned region,
   wherein the detection unit (30) is further configured to determine the diagnostic data in a plane of the eye (50) that corresponds to an object plane of the surgical microscope (10).

* * * * *